(12) United States Patent
Vogtmeier

(10) Patent No.: US 11,607,316 B2
(45) Date of Patent: Mar. 21, 2023

(54) PHYSICAL 3D ANATOMICAL STRUCTURE MODEL FABRICATION

(71) Applicant: KONINKLIJKE PHILIPS N.V., Eindhoven (NL)

(72) Inventor: Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 575 days.

(21) Appl. No.: 16/070,570

(22) PCT Filed: Feb. 13, 2017

(86) PCT No.: PCT/EP2017/053119
§ 371 (c)(1),
(2) Date: Jul. 17, 2018

(87) PCT Pub. No.: WO2017/140611
PCT Pub. Date: Aug. 24, 2017

(65) Prior Publication Data
US 2019/0021865 A1 Jan. 24, 2019

(30) Foreign Application Priority Data
Feb. 17, 2016 (EP) .................................. 16156094

(51) Int. Cl.
*A61F 2/30* (2006.01)
*A61B 5/107* (2006.01)
(Continued)

(52) U.S. Cl.
CPC .......... *A61F 2/30942* (2013.01); *A61B 5/107* (2013.01); *A61B 6/032* (2013.01); *A61B 6/505* (2013.01); *A61B 6/52* (2013.01); *A61B 6/5205* (2013.01); *A61B 6/5217* (2013.01); *A61B 6/545* (2013.01); *A61B 34/10* (2016.02); *A61F 2/28* (2013.01); *G09B 23/30* (2013.01);
(Continued)

(58) Field of Classification Search
CPC ............ A61F 2/28; A61B 34/10; G09B 23/30
USPC .......................................................... 700/98
See application file for complete search history.

(56) References Cited

U.S. PATENT DOCUMENTS

| 4,558,425 A | 12/1985 | Yamamoto |
| 7,371,067 B2 * | 5/2008 | Anderson ................. A61F 2/07 434/262 |

(Continued)

FOREIGN PATENT DOCUMENTS

| CN | 104739548 A | 7/2015 |
| JP | 2003265462 A | 9/2003 |

(Continued)

*Primary Examiner* — Md Azad
(74) *Attorney, Agent, or Firm* — Larry Liberchuk

(57) ABSTRACT

In one aspect of the invention a system and method is claimed for providing model parameters for three dimensional fabrication of anatomical structures by obtaining and reconstructing three dimensional image data with a medical imager wherein imaging acquisition parameters of the imaging system and/or reconstruction input parameters of the reconstructor are optimized for maximum geometry precision. Advantageously, the imaging system is further configured to obtain material and/or functional information of the anatomical structure model and that material information is used to incorporate the material information in the anatomical model.

19 Claims, 1 Drawing Sheet

(51) Int. Cl.
    *A61B 6/00*          (2006.01)
    *A61F 2/28*          (2006.01)
    *G09B 23/30*        (2006.01)
    *A61B 6/03*          (2006.01)
    *A61B 34/10*        (2016.01)

(52) U.S. Cl.
    CPC ............... *A61B 6/482* (2013.01); *A61B 6/484* (2013.01); *A61B 2034/105* (2016.02); *A61F 2002/30948* (2013.01); *A61F 2002/30962* (2013.01)

(56) References Cited

U.S. PATENT DOCUMENTS

| | | | |
|---|---|---|---|
| 10,064,686 B2 | 9/2018 | McKinnon | |
| 2006/0104409 A1 | 5/2006 | Bouman | |
| 2009/0010507 A1* | 1/2009 | Geng | G06T 7/593 |
| | | | 382/128 |
| 2013/0071001 A1* | 3/2013 | Waechter-Stehle | A61B 6/12 |
| | | | 382/132 |
| 2014/0017651 A1* | 1/2014 | Sugimoto | G09B 23/30 |
| | | | 434/272 |
| 2016/0275703 A1* | 9/2016 | Mariampillai | A61B 6/03 |
| 2018/0070902 A1* | 3/2018 | Lin | A61B 6/486 |
| 2018/0150929 A1* | 5/2018 | Pheiffer | G06T 7/30 |

FOREIGN PATENT DOCUMENTS

| | | |
|---|---|---|
| JP | 2015092999 A | 5/2015 |
| WO | 2015/074158 | 5/2015 |

\* cited by examiner

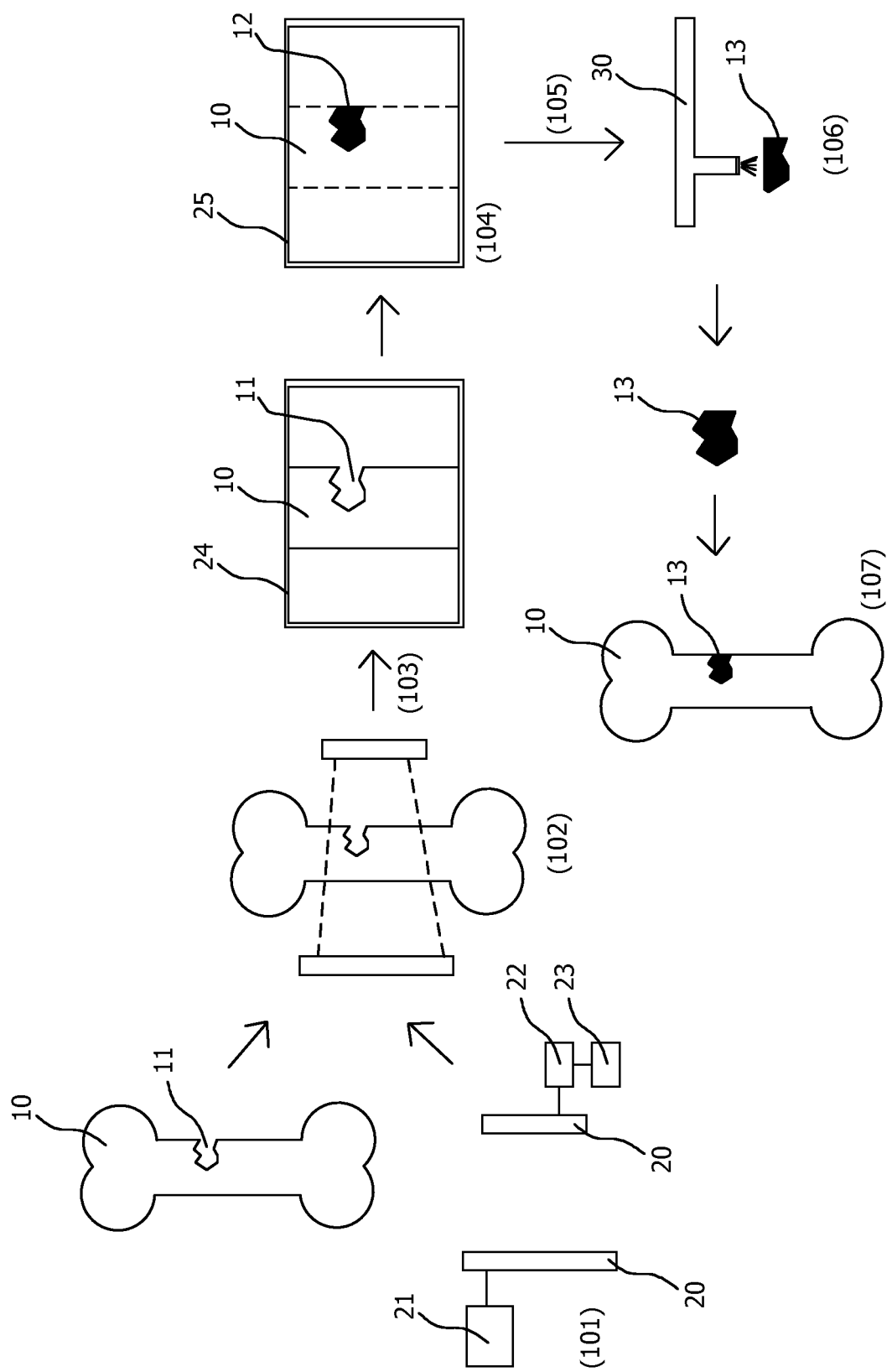

PHYSICAL 3D ANATOMICAL STRUCTURE MODEL FABRICATION

CROSS REFERENCE TO RELATED APPLICATIONS

This application is the U.S. National Phase application under 35 U.S.C. § 371 of International Application No. PCT/EP2017/053119, filed Feb. 13, 2017, published as WO 2017/140611 on Aug. 24, 2017, which claims the benefit of European Patent Application Number 16156094.1 filed Feb. 17, 2016. These applications are hereby incorporated by reference herein.

FIELD OF THE INVENTION

The present invention generally relates to a system and method for providing 3D (three dimensional) model parameters for fabricating a physical 3D anatomical structure model, a device and method for fabricating the physical 3D anatomical structure model and a computer program product.

BACKGROUND OF THE INVENTION

Anatomical models used for implants (e.g. skull parts, hip, knee, teeth implants) or for study of a patient are known and are fabricated in various manners, such as sculpting, casting, etching, etc. More recently anatomical parts have also been fabricated with 3D printing.

For all fabrication techniques it is important to obtain relevant anatomical data of an anatomy of interest of a patient that is precise and reliable enough to base a fabricated anatomical model on. Usually DICOM (Digital Imaging and Communications in Medicine) data libraries are used to obtain anatomical data, but this does not guarantee a match for a personalized anatomical model relating to a particular patient. WO2015/074158A1 discloses using computed tomography imaging to obtain geometric information of the anatomy of interest of the patient.

Geometric data (either from a DICOM library or a CT scan) is then converted to data that may directly or indirectly be used to fabricate the model. For instance, the geometric data is converted into 3D CAD (Computer Aided Design) data that may be directly fed to a fabrication device, such as a 3D printer. Alternatively, the geometric data may be first processed by another device and then used in a 3D model fabrication process.

It is a problem however to obtain reproducible and accurate geometric data from medical imaging, because most scanners are not operated such as to obtain a highest possible geometric precision.

SUMMARY OF THE INVENTION

The present invention intends to address the above mentioned drawbacks and allow a more precise and versatile fabrication of anatomical models.

Embodiments according to the present invention are directed to a system for providing 3D model parameters for fabricating a physical 3D anatomical model. The system comprises an imaging system is configured to acquire three dimensional image data of an anatomical structure, a reconstructor for reconstructing the acquired three dimensional image data into 3D model parameters; and a 3D model providing unit 23 for directly or indirectly providing the 3D model parameters to a device for fabricating the physical 3D anatomical model. A parameter provider for providing the optimized parameters provides imaging acquisition parameters of the imaging system and/or reconstruction input parameters of the reconstructor that are optimized for maximum geometry precision. This allows for fabricating a model with high geometrical accuracy.

In a preferred embodiment of the present the system the parameter provider is implemented as at least one selectable preset parameter setting. This offers ease of work for a user who just needs to select the optimized parameters for quick implementation of the present invention.

In a preferred embodiment of the present the system is further configured to obtain material information of the anatomical structure. Preferably the material information comprises one or more of material composition; structural distribution of material, such as material density or porosity; material energy information, such as radiation absorption or reflection properties; perfusion of other materials within the material, such as blood or contrast agent perfusion properties; tissue contrast information, such as contrast of or between hard and soft tissue materials; or temperature information. This additional information may be used to obtain more versatile anatomical models than with just geometrical information.

In a preferred embodiment the imaging system is a 3D x-ray imaging system, such as a computed tomography imaging system, preferably a spectral 3D x-ray imaging system or a phase-contrast x-ray imaging system; a magnetic resonance imaging system; an ultrasound imaging system; a positron emission tomography imaging system; a single photon emission computed tomography system; or combinations thereof.

The present invention is further directed to a device for fabricating the physical 3D anatomical structure model that is configured to fabricate the physical anatomical structure model 13 based on 3D model parameters received from a system according to the present invention. More precise anatomical models are obtained with such a device.

The device is further configured to adapt fabrication output based on material and/or functional properties within the 3D model parameters. Said output the fabrication output preferably includes different colors; color grades; transparency levels for different material parameters; variations in mechanical properties, such as stiffness or hardness; and/or imaging properties, such as ultrasound reflectivity, transmissivity or x-ray absorption. When present, the additional properties may improve accuracy and/or versatility of the anatomical models.

The device is preferably a 3D printer, which is a versatile fabrication device particularly suitable to obtain anatomical models with all the advantages of the present invention.

The invention is further directed towards methods corresponding with the system and device and a computer program product to perform said methods.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

BRIEF DESCRIPTION OF THE DRAWINGS

The present invention is illustrated by drawings of which
FIG. 1 shows a schematic representation of generating 3D parameters of an anatomical structure, fabricating said anatomical structure and using said anatomical insert.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

The invention is explained using FIG. 1, which is a highly schematic and basic overview of using medical imaging to fabricate anatomical inserts. In this non-limiting example the anatomical model is a bone insert and fabrication is performed by 3D printing. However, a skilled person would know how to adapt this example for other fabrication techniques and/or relevant anatomical models, such as for instance other bone structures, but also complete or sectional brain, heart, vascular system or organ models. The same FIGURE illustrates how to obtain non-insert anatomical models by simply not using the last step (107) after the model is obtained.

Physical anatomical models may be used for implantation into a body of a patient, to study general or patent specific anatomical issues, interventional therapy planning or for educational reasons. Obviously the models are most realistic when they are based on actual anatomy and in case of implantations or study of patient specific issues, this is even more important. Geometrical accuracy of an anatomical model is particularly important when it will be implanted in a body, for instance as a bone insert or a replacement implant such as hip, knee or dental implants. When the anatomical models are too large or small, even slightly, the fit may be poor, causing discomfort or even non-optimal functioning of the implant and/or a surgeon needs to correct the geometry during an intervention which prolongs the procedure and adds risk to the patient.

To achieve geometrical accuracy usually the anatomy of interest in the patient is medically scanned by a medical imager. Various types of medical imagers may be used depending on the anatomy and required accuracy and/or further functional or material information that may be obtained.

In FIG. 1 a bone 10 with a missing part 11, e.g. due to a fracture, birth defect or illness, is scanned 102 with a medical imager 20. In this example the medical imager is an imaging system 20 with a source and a detector, such as an x-ray, computed tomography (CT). Alternatively, other types of imagers may be used as well, such as magnetic resonance (MR) imaging system, positron emission tomography (PET), single photon emission computed tomography (SPECT) or in some cases an ultrasound imager. The type of medical imager is chosen based on the anatomy of interest. For hard structures, such as bones, x-ray imaging, particularly 3D x-ray imaging, such as C-arm x-ray or CT imaging, is particularly suitable. To obtain contrast between softer tissues MR or phase contrast x-ray or CT imaging may be more suitable. Ultrasound may be an option in cases where image quality is less critical or other functional information should be visualized.

For instance, for brain structures MR is the preferred modality. In this case the exact geometry of the brain is not used for implants, but for actual physical models that are used for exact planning and preparation of interventions. For example an exact position and volume of a tumor have to be shown to make correct decisions for surgical tools and procedures that have to be applied. For hard anatomies, such as bone structures and joints, CT imaging is the preferred technique, since this allows for optimized contrast between hard and soft tissue.

However, medical imagers are often not optimally tuned to obtain images with maximum geometrical precision and in many cases geometric information of medical images may deviate somewhat from the real situation. Because of this, patients may have to be rescanned, causing inconvenience, time delay and in some cases increased radiation exposure, or the anatomical model has to be redone based on corrected geometrical data or the model itself needs to be corrected by adding or removing material. Several iterations may be necessary to obtain an acceptable anatomical model, resulting in increased time to obtain the model and increased material use.

For instance, precision of an extracted medical imaging model depends on a type and model of the medical imager, parameter settings of a scan, but even more also on the reconstruction parameters and filter parameters. Also, the parameter settings might depend on or are optimized for the anatomy of interest. This is a big disadvantage as the precision of the model then is not always the same and deviations up to several millimeters may occur, which is insufficient accuracy for fabricating anatomical models, especially if these are later inserted into a body. For example, an exact geometry for a bone implant requires exact measurement of the existing bone structure. A discrepancy of several millimeters may make a fit of fabricated anatomical inserts problematic or even completely unsuitable, requiring post-fabrication corrections or even discarding of the inserts.

The present invention offers a solution to this by configuring an imaging system 20 to generate three dimensional image data 24 of the anatomical structure with acquisition and/or reconstruction parameters that were optimized for maximum geometry precision. The term maximum geometry precision should be read in the context of this application that geometry information is acquired at the highest geometry precision possible with the used medical imager, even at the cost of other parameters. An image parameter selection unit is configured to select the optimized imaging acquisition parameters of the imaging system and/or reconstruction input parameters of the reconstructor. This may be implemented in optimized scan acquisition parameters (e.g. radiation dose or distribution, filter optimization, detector sensitivity, etcetera) and/or input parameters reconstruction models that are optimized or even fully dedicated to obtain geometrical information. Embodiments of the present invention are therefore directed towards optimized settings for scan and acquisition parameters to obtain scan data that already are optimized for geometrical accuracy and/or settings to optimally reconstruct and process already acquired data for maximum geometrical accuracy. In an embodiment of the present invention the acquisition and/or reconstruction parameters are optimized to obtain imaging data with sharp edges. This may be implemented by using acquisition parameters that are known to result in hard edges or by using dedicated, or even no smoothing algorithms. Commonly edges are smoothed in imaging for improved visualization by such smoothing algorithms, but smoothing complicates determining geometric information and since there a multitude of smoothing algorithms, geometrical information obtained from one smoothing algorithm may not result in the same geometrical data as when another smoothing algorithm is used.

For example, an exact geometry for a bone implant requires the exact measurement of existing bone structure. So already scan acquisition parameters of the medical imager, e.g. a CT imaging system, may be optimized to have maximum contrast for bone structures versus tissue (optimized setting for kV and/or mA). Reconstruction and filtering parameters then may be optimized for best contrast at exactly the bone-to-tissue interface to enable precise segmentation and geometry extraction of the selected region of interest.

Motion of the anatomy of interest may lead to unprecise geometry data. Therefore, additional effort may be taken for reduction of motion artefacts and/or imperfections due to movements of the anatomy of interest during the scan. A combination of high temporal resolution in combination with high spatial resolution and optimized motion correction results in high precision of the geometry data.

Since each scanner modality, type and model, or even individual scanner, especially from different manufacturers, might have different optimized settings, and, because fabrication service providers, such as 3D printing services, only provide guidelines for the scan about which of the standard protocols should be used, it would be highly beneficial that the optimized parameters are available to a user of a certain scanner, for instance as a pre-set option that the user may select. This may be implemented for instance by offering a visible feature 21 in the control software or hardware, e.g. a "processing for 3D model" button or an otherwise selectable predefined setting that activates a protocol that causes the imager to use the optimized settings to achieve maximum geometry precision.

To determine an optimized acquisition protocol for a particular scanner, a dedicated geometry calibration with a precisely dimensioned three-dimensional phantom may be used to calibrate and validate the protocol settings. This may even be optimized for special material selections.

Adaptation of spatial resolution at the interfaces of the anatomy or region of interest may be optimized to provide the best data for conversion to 3D CAD data formats that are used for modelling and fabrication of anatomical model to transfer to the fabrication devices (e.g. STL (Stereolithography format).

External service providers for fabricating an anatomical model, such as for instance 3D printing companies, can only use the dataset they receive as it comes from the imaging device without knowing optimizations and the variability of the data, so it may be beneficial to standardize geometrical information that is outputted from a medical imager, such that it may be directly used by any fabrication service provider.

It is an insight of the present invention that most scanner modalities or variations of each scanner modality are able to provide more than just geometrical information, but also material information and that this additional material information may be used advantageously to not only improve the precision and quality of physical anatomical models, but also use this additional material information in the physical anatomical models for providing additional information or highlighting certain facets of the anatomy.

For instance, some modalities are particularly suitable to obtain material information of a functional object (e.g. a tumor) besides geometrical information. This information may then be used in fabricating the anatomical model, for instance by highlighting or color grading the material information of the functional object (or the whole anatomical object) in the physical model or providing an extracted separate version of the functional object, which is especially useful if the functional object is embedded within the anatomy of interest (e.g. a tumor within a liver, lung, brain, etc.) and needs to be studied. A particularly interesting embodiment would be to fabricate the main anatomical model in transparent material and the functional object in color within, for instance a tumor and supply blood vessel and use color grading to show blood penetration towards and in the tumor. For instance, in perfusion imaging actual blood flow information may be used for color mapping with high geometry precision.

Also the flexibility of the anatomical model may be fabricated according to the original anatomy, e.g. an organ, if the additional material data is used in combination with the geometry information. In one embodiment mapping of a material parameter is mapped to dedicated segmented organ regions. This allows for automatic mapping of the measured property (e.g. via spectral CT) to the segmented regions in the 3D model data, such as a CAD model. This leads to exact 'look-and-feel' models made for a certain purpose, e.g. a same tactile experience (feeling') for a surgeon to cut into the tissue of the model for training and later in a real interventional procedure.

The additional material information may also be of interest for anatomical models that are to be implanted, e.g. using the determined bone structure density to estimate the stability of the anatomical model. Generally, this data may depend also on the orientation and position of the anatomy during imaging (e.g. the position of a patient on a patient support in a medical imager). Also this information is available and is preferably be used. Further, also involuntary anatomical movements, such as the phase of the heartbeat and/or the breathing phase of the lung, are known and the best phase may be selected for the data acquisition.

X-ray imaging, and particularly CT imaging, is particularly useful to obtain material information besides geometrical information. With quantitative x-ray or CT imaging information on material density or porosity and material x-ray absorption information may be obtained (e.g. by analyzing the Houndsfield unit values for the anatomy of interest). With k-edge x-ray or CT imaging contrast agent perfusion and flow information within an anatomy of interest may be determined. X-ray and CT imaging is particularly good for imaging hard tissue anatomies, but with phase contrast x-ray or CT imaging enhanced soft tissue contrast is obtained, which may improve geometrical information, but also further opens up using x-ray or CT imaging for soft tissue anatomies. Dark field x-ray and CT imaging may provide additional information on material structure and tissue or bone density. In an embodiment the anatomical model is based on CT imaging information, wherein the anatomical model is fabricated based on Houndsfield unit information, e.g. by printing or otherwise fabricating with color information based on the Houndsfield values, e.g. more transparent for a region with a low Houndsfield unit value and darker for a region with a high Houndsfield unit value.

MR imaging may provide various material properties of tissue, especially for soft tissue or radiation sensitive anatomies. PET and SPECT imaging are particularly useful for obtaining material information of functional objects, such as tumors, as described previously. Even though ultrasound provides less high resolution, which limits its use for obtaining geometrical information as precise as with the previously mentioned imaging modalities, but in some cases ultrasound is adequate enough for obtaining geometrical information, while additional information such as transmission, reflection and even temperature of the anatomy of interest may be obtained simultaneously. Other modalities available to the skilled person are contemplated as well, as are combinations of different modalities.

The system for providing 3D model parameters for fabricating a physical 3D anatomical model according to the present invention and the device or fabricating the physical 3D anatomical structure model may be integrated in one combined system.

The quality of the fabricated model depends on the 3D model parameters. External fabrication service suppliers only work with the DICOM data is it actually comes out of the system, which only the imaging device manufacturer has influence on providing this data. Standardization of said data would be highly beneficial to allow for higher quality models and better comparison between models based on different imaging data. Linked to the available geometrical and additional material information data from the imaging device is availability of optimized processing, transport and storage of the data in a, preferably standardized, "extended DICOM" or other format to make it available for segmentation, CAD processing optimized for the fabrication purpose. Improved data transport and a potential new data interface to the fabrication-hardware controlling processing, material mix and color as well as material properties of the anatomical model.

The additional material information is inherently available with most of the performed scans anyway, but in the prior art is not used in fabrication of the anatomical models. It is therefore an advantage of the present invention which not only improves the quality of the models, it also extends the possibilities that such physical anatomical offer to physicians for treatment or study, while no further scans or tests are necessary. For a physician it is very interesting to have a physical representation of this additional material information.

In FIG. 1, after providing 101 optimized acquisition or reconstruction parameters from a parameter provider 21 and scanning 102 the anatomy of interest, obtained 3D image data is reconstructed by a reconstructor 22 to 3D model data 24, which includes geometrical information, but preferably also includes additional material and/or functional information. Next the reconstructed data may be processed 104 by a 3D model provider 23, for instance to segment a particular area of interest 12 or to obtain geometric information 25 for fabrication an implant and to convert the 3D image data to 3D fabrication input data. The 3D fabrication input data is transferred 105 to a 3D fabrication device 30, such as a 3D printer which fabricates 106 the anatomical model using the geometrical data and, optionally, the additional material information. The anatomical model 13 may then be used for study or to be implanted 107, for instance as a bone insert for the missing part 11 of the exemplary bone 10 used in FIG. 1 to illustrate the invention.

Optimized material processing for 3D fabrication and for implant-surgery provides very valuable additional information that on the one hand side may be visualized for the physician and on the other side could be used in the enhanced CAD data file that is used for more exact modelling of the 3D object. The material information may further be used to optimize or adapt to a body interface material.

Another application of the optimized imaging parameters and resulting image data 24 is that these may be used for industrial inspection.

Use of additional material information next to pure geometrical information also benefits from predetermined optimized settings that are made available to the user, but the advantages already inherently exist, even without optimized settings.

A device 30 for fabrication of anatomical models according to the present invention preferably comprises a 3D printer. 3D printing is a versatile fabrication technique for an ever extending range of materials that allows for many, if not all, of the advantages of the present invention to be implemented, such as using different colors, color grades, transparency levels or even different materials for fabricating different anatomical parts or different material properties of different anatomical areas. For instance, also functional properties may be mapped to different colored sections or color grading, such as blood flow, tumor concentration, hot spots, etc. Also variations in mechanical properties of the anatomical model may be implemented, such as stiffness or hardness. Further, imaging properties, such ultrasound reflectivity, transmissivity, X-ray absorption may be represented in the model visually or mechanically.

The optimized scan parameters are preferably implemented in computer software, which preferably also includes providing instructions for a device to fabricate the anatomical models.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for providing 3D (three dimensional) model parameters for fabricating a physical 3D anatomical model, comprising:
   an imaging system configured to acquire 3D image data of an anatomical structure;
   a reconstructor configured to reconstruct the acquired 3D image data into 3D model parameters;
   a 3D model provider configured to provide the 3D model parameters to a device for fabricating the physical 3D anatomical model,
   a parameter provider configured to provide at least one of:
      imaging acquisition parameters of the imaging system; and
      reconstruction input parameters of the reconstructor, wherein at least one of the imaging acquisition parameters and reconstruction input parameters are optimized for maximum geometry precision; and wherein the imaging system is further configured to obtain material information of the anatomical structure, the material information including tissue contrast information that comprises contrast of or between hard and soft tissue materials.

2. The system according to claim 1, wherein the parameter provider is implemented as at least one selectable preset parameter setting.

3. The system according to claim 1, wherein the material information comprises one or more of material composition; structural distribution of material; material energy information; perfusion of other materials within the material; or temperature information.

4. The system according to claim 1 wherein the imaging system is a 3D x-ray imaging system; a magnetic resonance imaging system; an ultrasound imaging system; a positron emission tomography imaging system; a single photon emission computed tomography system; or combinations thereof.

5. The system according to claim 3,
wherein the structural distribution of material comprises material density or porosity;
wherein the material energy information comprises radiation absorption or reflection properties; and
wherein the perfusion of other materials within the material comprises blood or contrast agent perfusion properties.

6. The system according to claim 4, wherein the 3D x-ray imaging system comprises a spectral 3D x-ray imaging system or a phase-contrast x-ray imaging system.

7. A device for fabricating a physical 3D (three dimensional) anatomical structure model based on 3D model parameters received from an imaging system configured to acquire 3D image data of an anatomical structure, the device comprising:
a reconstructor configured to reconstruct the acquired 3D image data into the 3D model parameters;
a 3D model provider configured to provide the 3D model parameters;
a parameter provider configured to provide at least one of:
imaging acquisition parameters of the imaging system; and
reconstruction input parameters of the reconstructor,
wherein at least one of the imaging acquisition parameters and reconstruction input parameters are optimized for maximum geometry precision; and
wherein the device is further configured to obtain material information of the anatomical structure, the material information including tissue contrast information that comprises contrast of or between hard and soft tissue materials.

8. The device according to claim 7, wherein the device is further configured to adapt fabrication output based on at least one of material and functional properties within the 3D model parameters.

9. The device according to claim 8, wherein the fabrication output includes at least one of different colors; color grades; transparency levels for different material parameters; variations in mechanical properties; and imaging properties.

10. The device according to claim 7 further comprising a 3D printer.

11. The device according to claim 9,
wherein the mechanical properties comprise stiffness or hardness; and
wherein the imaging properties comprise ultrasound reflectivity, transmissivity or x-ray absorption.

12. A method for providing 3D (three dimensional) model parameters for 3D fabrication of anatomical structures, the method comprising:
obtaining 3D image data of an anatomical structure, wherein the image data is obtained with a medical imager that is configured to acquire the 3D image data;
reconstructing, by a reconstructor, the acquired 3D image data into 3D model parameters; and
providing the 3D model parameters to a device for fabricating a physical 3D anatomical structure model,
wherein at least one of imaging acquisition parameters of an imaging system and reconstruction input parameters of the reconstructor are optimized for maximum geometry precision, and wherein the imaging system is further configured to obtain material information of the anatomical structure, the material information including tissue contrast information that comprises contrast of or between hard and soft tissue materials.

13. The method according to claim 12, wherein the medical imager is further configured to obtain functional information of the physical 3D anatomical structure model.

14. The method according to claim 13, wherein the material information comprises one or more of material composition; structural distribution of material; material energy information; perfusion of other materials within the material; or temperature information.

15. The method according to claim 13, wherein the physical 3D anatomical structure model comprises at least one of material and information of the anatomical model.

16. A method for fabricating a physical 3D anatomical structure model, the method comprising:
the method according to claim 12; and
fabricating the physical 3D anatomical structure model based on the 3D model parameters.

17. A non-transitory computer readable medium comprising a program element for providing a system for providing 3D (three dimensional) model parameters for fabricating a physical 3D anatomical structure model, which, when being executed by processor circuitry, the system is configured to perform the method according to claim 16.

18. The method according to claim 14,
wherein the structural distribution of material comprises material density;
wherein the material energy information comprises radiation absorption or reflection properties; and
wherein perfusion of other materials within the material comprises blood or contrast agent perfusion properties.

19. The method according to claim 16, wherein the physical 3D anatomical structure model is fabricated by 3D printing.

* * * * *